(12) United States Patent
Gulevich et al.

(10) Patent No.: US 7,465,821 B2
(45) Date of Patent: Dec. 16, 2008

(54) PROCESS FOR PREPARING ALKYLIDENE-SUBSTITUTED-1, 4-DIONS DERIVATIVES

(75) Inventors: Yuri V. Gulevich, Ferrara (IT); Giampiero Morini, Padua (IT)

(73) Assignee: Basell Poliolefine Italia S.p.A., Milan (IT)

( * ) Notice: Subject to any disclaimer, the term of this patent is extended or adjusted under 35 U.S.C. 154(b) by 347 days.

(21) Appl. No.: 10/491,560

(22) PCT Filed: Jul. 9, 2003

(86) PCT No.: PCT/EP03/07410

§ 371 (c)(1), (2), (4) Date: Apr. 2, 2004

(87) PCT Pub. No.: WO2004/014838

PCT Pub. Date: Feb. 19, 2004

(65) Prior Publication Data

US 2005/0080290 A1 Apr. 14, 2005

Related U.S. Application Data

(60) Provisional application No. 60/401,208, filed on Aug. 5, 2002.

(51) Int. Cl.
*C07C 69/52* (2006.01)
(52) U.S. Cl. .................................... 560/190
(58) Field of Classification Search .................... 568/31
See application file for complete search history.

(56) References Cited

U.S. PATENT DOCUMENTS

| RE36,718 E | * | 5/2000 | Mitsuda |
| 7,005,487 B2 | | 2/2006 | Balbontin et al. |
| 2005/0113599 A1 | | 5/2005 | Gulevich et al. |

FOREIGN PATENT DOCUMENTS

| EP | 760355 | 3/1977 |
| EP | 0760355 | 3/1997 |
| WO | WO 2004/005359 | 1/2004 |

OTHER PUBLICATIONS

Roberto Ballini, and Giovanna Bosica A Direct Method for the Synthesis of Polyfunctionalized Unsaturated Carbonyl Derivatives by Michael Addition of Nitroalkanes to Enediones with the Help of DBU Tetrahedron vol. 51, No. 14, pp. 4213-4222, 1995.*
Roberto Ballini, Giovanna Bosica, Marco Damiani, and Paolo Righi Nitroalkanes as a New Source of 2-Alkylidene-1,4-diols in Two Steps Tetrahedron 55 (1999) 13451-13456.*
N. Lalitha, U.T. Bhalerao and D.S. Iyengar Sequential Addition of 2-Potassio-2-nitropropane and Oxygen to 4-Arylidene-oxazol-5-one: A New Method for 2-Aryl Butenoic Acid Imides J.Chem. Soc., Chemical Communications Issue 13 1991, p. 897-899.*

(Continued)

Primary Examiner—Paul A Zucker
(74) Attorney, Agent, or Firm—Jarrod N. Raphael

(57) ABSTRACT

A process for the preparation of an monoalkylidene substituted 1,4-dions derivatives of formula (Ia) or (Ib) or a mixture of (Ia) and (Ib): wherein: $R^1$, $R^2$ and $R^3$, equal to or different from each other, are hydrogen atoms or $C_1$-$C_{20}$ hydrocarbon groups: $T^1$ and $T^2$, equal to or different from each other, are $OR^4$. $R^4$, $NR^4_2$, $SR^4$ or $PR^4_2$; or $T^1$ and $T^2$ can be fused in an oxygen atom or a $NR^4$ group; said process comprises the step of reacting a compound of formula (II), with a compound of formula (IIIa) or (IIIb), in the presence of at least one equivalent with respect to the compound of formula (IIIa) or (IIIb) of a salts of a base or a neutral base at a temperature higher than 70° C.

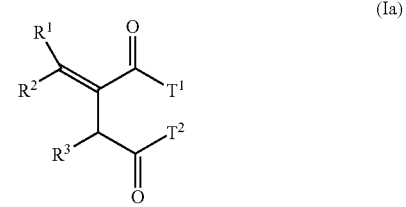

(Ia)

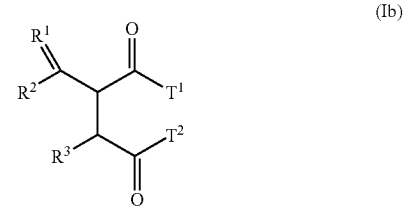

(Ib)

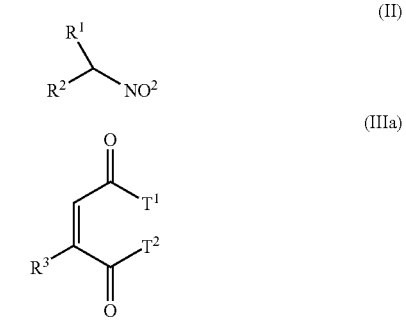

(II)

(IIIa)

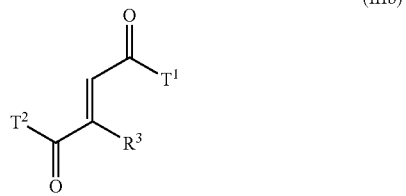

(IIIb)

22 Claims, No Drawings

OTHER PUBLICATIONS

Patent Application No. 01202184.6 (PCT/EP+02/0609)—Process for Preparing Alkylidene Substituted Succinic Esters; filed Jul. 6, 2001 by Basell Technology Company B.V.

C. G. Overberger et al., "The Preparation of 2-Alkyl-1, 4-butanediols;" *J. Am. Chem. Soc.*; vol. 71, p. 3618-3621 (1949).

M. C. Kloetzel, "Reactions of Nitroparaffins. II. Addition of Nitroparaffins to Unsaturated Esters;" *J. Am. Chem. Soc.*, vol. 70, p. 3571-3576 (1948).

R. Ballini et al., "The Michael Reaction of Nitroalkanes with Conjugated Enones in Aqueous Media;" *Tetrahedron Letters*, vol. 37(44), p. 8027-8030 (1996) XP-004031034.

R. Ballini et al., "Nitroaldol Reaction in Aqueous Media: An Important Improvement of The Henry Reaction;" *J. of Org. Chem., American Chemical Society*, vol. 62(2), p. 425-427 (1997) XP-000640627.

R. Ballini et al., "A Direct Method for the Synthesis of Polyfunctionalized Unsaturated Carbonyl Derivatives by Michael Addition of Nitroalkanes to Enediones with the Help of DBU;" *Tetrahedron*, vol. 51(14), p. 4213-4222 (1995).

R. Ballini et al., "Synthesis of (*E*)-3-Alkylidenepyrrolidines by Nucleophilic Ring Closure of (*E*)-2-Alkylidene-1,4-diol Derivatives;" *Eur. J. Org. Chem.*, p. 2927-2931 (2000).

R. Ballini et al., "Michael Addition of Nitroalkanes to Dimethyl Maleate with DBU. A New Direct Method of the Synthesis of Polyfunctionalized $\alpha,\beta$-Unsaturated Esters;" Tetrahedron Letters, vol. 35(49), p. 9247-9250 (1994).

R. C. Larock, "Comprehensive Organic Transformations, A Guide to Functional Group Preparations—Second Edition;" (Table of Contents) published by Wiley-VCH, p. xv-xxxiv (1999).

S. R. Sandler et al., "Organic Functional Group Preparations, vol. 12-I, Second Edition;" (Table of Contents), published by Academic Press, Inc., p. v-ix (1983).

S. R. Sandler et al., "Organic Functional Group Preparations, vol. 12-II, Second Edition;" (Table of Contents), published by Academic Press, Inc., p. v-viii (1986).

S. R. Sandler et al., "Organic Functional Group Preparations, vol. 12-III, Second Edition;" (Table of Contents), published by Academic Press, Inc., p. v-vii (1998).

* cited by examiner

PROCESS FOR PREPARING ALKYLIDENE-SUBSTITUTED-1,4-DIONS DERIVATIVES

This application is the U.S. national phase of International Application PCT/EP2003/007410, filed Jul. 9, 2003.

The present invention relates to a novel process for preparing 1,4 dions derivatives substituted with alkylidene groups. These compounds are easily convertible into the corresponding alkyl-substituted derivatives that are used as electron donor compounds in the preparation of Ziegler-Natta heterogeneous catalysts for the polymerization of olefins.

Transformation of the alkylidene-substituted 1,4 dions derivatives into the matching alkyl-substituted compounds is normally a clean reaction with an almost quantitative yield. Therefore, in order to industrially produce these compounds in an industrially exploitable way, it is necessary to have an economically advantageous process for the production of the corresponding alkylidene-substituted compounds. By the term "economically advantageous" it is meant a process able to give the target product in good yields and acceptable purity by the use of such reagents and conditions that the process is as smooth and cheap as possible. Monoalkylidene-substituted succinic acid esters are known in the art for example by the article from C. G. Overberg, C. W. Roberts, *J. Am. Chem. Soc.*, Vol. 71, pp. 3618-3621, 1949. This document describes the preparation of several types of 2-alkylidene-substituted succinic acid esters carrying out the Stobbe reaction using potassium tert-butoxide as a base and tert-butanol as a solvent. The starting diethyl succinate was used in excess with respect to both the starting ketone (25%) and the base, which in turn was in excess (about 10%) with respect to the ketone. The highest yields were obtained using acetone as a ketone and were 92% with respect to the ketone, but much lower with respect to the succinate (76%). Most importantly however, a long and complicate work-up (solvent distillation, acidification with diluted HCl to pH=3, complete solvent distillation, extraction with ether, extraction of the ethereal solution with basic water, acidification of basic water with HCl conc., extraction with ether, anhydrification, solvent evaporation) of the reaction was needed in order to separate the non-reacted reagents from the final product. This clearly would make such process very costly if carried out on a large scale.

More recently, EP 760,355 disclosed the preparation of a 2-alkylidene-substituted succinate via the Stobbe reaction and using cycloheptanone as starting ketone. The base was potassium tert-butoxide and the solvent was dimethylformamide (DMF). Again, the yields were high with respect to the ketone (97%) but lower with respect to the succinate (75%), which was used in excess (34%). Taking also into account the excess of base used it is possible to understand that also in this case the work-up of the reaction in order to obtain only the desired product would be troublesome on a large scale.

In J. Am. Chem Soc., Vol. 70, pp. 3571-3576, 1948 Kloetzel proposed a different approach for the preparation of 2-alkylidene-substituted succinates. The process comprises the reaction of fumaric acid ester with nitroalkane in the presence of diethylamine. While the yields were acceptable, the reaction required a very long time, 14-18 days, the starting nitroalkane was used in large excess (300%) with respect to the fumaric acid ester, and the isolation of the product was complicated due to the presence of N-nitrosodiethylamine, a highly hazardous compound, and nitroalkylsuccinic acid ester, not fully utilised reaction intermediate.

In *Tetrahedron*, Vol. 51, no. 14, pp. 4213-4222, 1995 Ballini used 1,8-diazabiciclo[5.4.0]undec-7-ene (DBU) as a base for a similar reaction of maleic acid ester with nitroalkane to obtain 2-alkylidene-substituted succinates. More recently, in Eur. J. Org. Chem., pp. 2927-2931, 2000, Ballini expanded the scope of this reaction to include also preparation of 2-alkylidene-substituted 4-oxo-butanoates and 1,4-diketones by the DBU-promoted reaction of nitroalkanes with the corresponding 2-en-1,4-dions. According to these documents the reaction times are quite short and the yields of the corresponding 2-alkylidene-1,4-dions (succinates, 4-oxo-butanoates and 1,4-diketones) are quite high. However the results of this reaction can be improved in terms of both yield and purity of the final product. In *Tetrahedron Letters*, Vol. 35, no. 49, pp. 9247-9250, 1994 Ballini tried also other bases such as basic alumina, Amberlyst A21 and triethylamine but he stated that the best reactant was DBU. In all these documents the reactions are carried oout at room temperature and no suggestion about a possible temperature effect in terms of yields is given.

Thus there is a need to find a process for preparing in high yields and in a simple and cheap way 2-alkylidene-substituted-1,4-dions derivatives.

The applicant has now discovered that such a desired process is feasible when the reaction between nitroalkane and 2-en-1,4-dions is carried out at high temperature.

It is therefore an object of the present invention a process for the preparation of 2-alkylidene-1,4-dions, derivatives, of formula (Ia) or (Ib) or a mixture of (Ia) and (Ib):

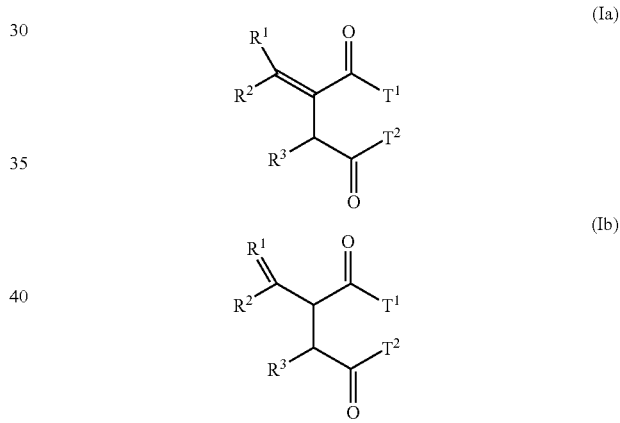

wherein:

$R^1$, $R^2$ and $R^3$, equal to or different from each other, are hydrogen atoms or $C_1$-$C_{20}$ hydrocarbon groups; optionally containing heteroatoms belonging to group 13-17 of the periodic table; or $R^1$ and $R^2$ can join together to form a saturated or unsaturated $C_3$-$C_{10}$ ring optionally containing heteroatoms belonging to group 13-17 of the periodic table; with the proviso that when $R^1$ and $R^2$ are both hydrogen atoms, only compounds of formula (Ia) are obtained;

preferably $R^3$ is a hydrogen atom, a linear or branched, saturated or unsaturated $C_1$-$C_{15}$ alkyl, $C_3$-$C_{10}$ cycloalkyl, $C_6$-$C_{10}$ aryl, $C_7$-$C_{12}$ alkylaryl or $C_7$-$C_{12}$ arylalkyl radical; more preferably $R^3$ is a hydrogen atom, a linear or secondary $C_1$-$C_8$ alkyl or $C_5$-$C_7$ cycloalkyl group such as methyl, ethyl, isobutyl or cyclohexyl; even more preferably $R^3$ is a hydrogen atom;

$T^1$ and $T^2$, equal to or different from each other, are H, $OR^4$, $R^4$, $NR^4{}_2$, $SR^4$ or $PR^4{}_2$; or $T^1$ and $T^2$ can be fused in an oxygen atom or a $NR^4$ group to form for example compounds of formula (Ic) or (Id):

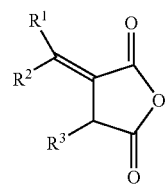

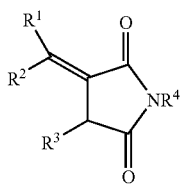

and the corresponding double bonds isomers;

$R^4$, equal to or different from each other, are a $C_1$-$C_{20}$ hydrocarbon group, optionally containing one or more heteroatoms belonging to group 13-17 of the periodic table;

preferably $R^4$ is a linear or branched $C_1$-$C_{20}$ alkyl, $C_3$-$C_{10}$ cycloalkyl, $C_6$-$C_{10}$ aryl or a $C_7$-$C_{12}$ alkylaryl group; more preferably $R^4$ is a linear or branched $C_1$-$C_8$ alkyl or $C_5$-$C_{10}$ cycloalkyl group such as methyl, ethyl, isobutyl, tert-butyl or cyclohexyl;

preferably $T^1$ and $T^2$ are $OR^4$, $R^4$, $NR^4{}_2$, $SR^4$; more preferably $T^1$ and $T^2$ are $OR^4$;

said process comprises the step of reacting a compound of formula (II)

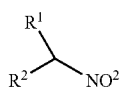

with a compound of formula (IIIa) or (IIIb)

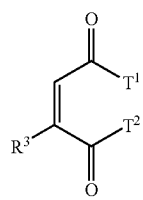

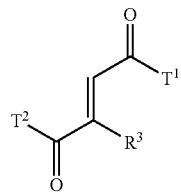

in the presence of at least one equivalent with respect to the compound of formula (IIIa) or (IIIb) of a salts of a base or a neutral base at a temperature higher than 70° C.

For the purpose of the present invention "one equivalent" means the same amount of basic functionality i.e. the capability to accept an acidic proton. Thus for example one equivalent of $K_2CO_3$ means that only 0.5 mole of $K_2CO_3$ per mole of compound of formula (IIIa) or (IIIb) are used, for the reason that the anion $CO_3{}^{2-}$ is able to accept 2 acidic protons. In the same way, for example, one equivalent of $KHCO_3$ means that one mole of $KHCO_3$ is used per one mole of compound of formula (IIIa) or (IIIb) for the reason that the anion $HCO_3{}^-$ is able to accept one acidic proton.

Non limitative examples of a salts of a base or a neutral base are:

(i) oxides of metal if group 1-13 of the periodic table, preferably from groups 1, 2 and 13; such as CaO, BaO and $Al_2O_3$;

(ii) compounds of formula $NR^9{}_3$ wherein $R^9$ equal to or different from each other, are hydrogen atom, or a linear or branched, saturated or unsaturated, $C_1$-$C_{10}$ allyl, $C_6$-$C_{20}$ aryl, $C_7$-$C_{20}$ arylalkyl or $C_7$-$C_{20}$ alkylaryl groups, optionally containing O, S, N, P, Si or halogen atoms, or two or more $R^9$ form one or more saturated or unsaturated 4 to 7 membered rings, optionally containing O, S, N, P or Si atoms, that can bear substituents; when this ring is aromatic one $R^9$ can also be a bond part of a double bond to form for example compound like pyridine, or pyrazine; preferably $R^9$ is a linear or branched, saturated or unsaturated, $C_1$-$C_{10}$ alkyl group or two $R^9$ form a 5 or 6 membered ring such as pyrrole, or the compound of formula $NR^9{}_3$ is of 1,8-diazabiciclo[5.4.0]undec-7-ene (DBU);

(iii) compounds of formula $MT_j$ wherein M is a metal of groups 1-12 of the periodic table, or a group ($NR^9{}_4$) wherein $R^9$ as been described above, preferably M is a metal of groups 1,2 of the periodic table, more preferably M is sodium or potassium; T is H, $F^-$, $OH^-$, $HCO3^-$; $RO^-$ or $RC(O)O^-$ wherein R is a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radical, optionally containing one or more halogen atoms; j is equal to the valence of the metal M or 1 in the case M is $(NR^9{}_4)^+$;

(iv) carbonates of metal M wherein M is a metal of groups 1-12 of the periodic table, preferably M is a metal of groups 1, 2 of the periodic table, more preferably M is sodium or potassium.

Preferred salts are $K_2CO_3$; $KHCO_3$; $Na_2CO_3$; $NaHCO_3$;

Example of salts of a base or, neutral base salts that can be used in the present invention are:

$Li_2CO_3$; $K_2CO_3$; $Na_2CO_3$; $MgCO_3$; $CaCO_3$, $BaCO_3$;

$LiHCO3$; $KHCO_3$; $NaHCO_3$; $Mg(HCO_3)_2$; $Ca(HCO_3)_2$, $Ba(HCO_3)_2$;

$LiOCH_3$; $KOCH_3$; $NaOCH_3$; $LiOCH_2CH_3$; $KOCH_2CH_3$; $NaOCH_2CH_3$;

$LiOC(O)CH_3$; $KOC(O)CH_3$; $NaOC(O)CH_3$; $LiOC(O)CH_2CH_3$; $KOC(O)CH_2CH_3$;

$NaOC(O)CH_2CH_3$; NaOH; KOH; $CH_3ONa$; $CH_3OK$; CaO; BaO; LH; NaH; $(CH_3CH_2)_3N$; $NH_3$.

The amount of the salt of a base or of the neutral base to be used in the process is at least one equivalent with respect to the compound of formula (IIIa) or (IIIb). Preferably the amount is between 1 and 4 equivalents, more preferably between 1 and 1.5.

Generally the molar ratio between the compounds of formula (II) and (IIIa) or (IIIb) ranges from 5 to 0.2, preferably from 1.5 to 0.5, more preferably from 1.2 to 1.

The reaction can be carried out both in protic and aprotic solvent, such as water, or alcohols for protic solvents and toluene, ethylbenzene, xylene, dimethylformammide (DMF), N,N-dimethylacetamide, 1-methyl-2-pyrrolidone, diethylether, tetrahydrofurane, acetonitrile, for aprotic solvents. As a general rule solvent having higher boiling point are preferred.

Otherwise the reaction can also be carried out without solvents when one or more reactants are in liquid phase.

As it has been explained, the above process is very suitable for obtaining the 2-alkylidene substituted-1,4-diones derivatives in very high yields. Moreover, the applicant found that by carrying out the process according to the above-mentioned conditions the work-up of the final reaction mixtures is very simple. In fact, in most of the cases the work-up comprises only a dilution of the reaction mixture with water and an extraction of the desired products with an appropriate organic solvent, which is then suitably removed.

One class of preferred compounds among those of formulas (Ia) or (Ib) is that in which $R^2$ is hydrogen and $R^1$ is selected from $C_4$-$C_{20}$ hydrocarbon groups. Among them, particularly preferred are the compounds in which $R^1$ is $C_1$-$C_8$ alkyl, $C_5$-$C_{10}$ cycloalkyl, $C_6$-$C_{10}$ aryl, $C_7$-$C_{12}$ alkylaryl or $C_7$-$C_{12}$ arylalkyl radical; even more preferred are the compounds in which $R^1$ is $C_1$-$C_8$ alkyl or $C_5$-$C_{10}$ cycloalkyl radical.

Another class of preferred compounds among those of formulas (Ia) or (Ib) is that in which both $R^1$ and $R^2$ are $C_1$-$C_{20}$ hydrocarbon groups, among them particularly preferred are the compounds in which $R^1$ and $R^2$, equal to or different from each other, are $C_1$-$C_8$ alkyl.

Examples of $R^1$ and $R^2$ are: methyl, ethyl, n-propyl, cyclobutyl, but-3-enyl, cyclopropyl, isopropyl, n-butyl, sec-butyl, tert-butyl, n-pentyl, isopentyl, sec-pentyl, 1-ethylpropyl, cyclohexyl, 4methylcyclohexyl, 2-methylcyclohexyl, 3-methylcyclohexyl, neo-pentyl, cyclopentyl.

The compounds in which both $R^1$ and $R^2$ are the same and chosen among methyl, ethyl or propyl are preferred. Also preferred are the compounds in which $R^1$ and $R^2$ are linked together to form a cycle containing from 3 to 10 carbon atoms such as cyclopentyl, cyclohexyl, or cycloheptyl.

In carrying out the process of the present invention the reactants can be brought into contact with each other according to any order whatsoever.

The temperature for carrying out the process ranges from 70 to 300° C., more typically from 80 to 220° C. and preferably from 150 to 200° C. The skilled in the art can easily select, within these ranges, the optimum temperature by taking into account parameters like the boiling temperature of the reaction medium, that of the starting compounds and the desired rate of the reaction.

The alkylidene-substituted-1,4-dions derivatives obtained with the process of the present invention can be converted into the corresponding alkyl-substituted derivatives with methods known in the art. These final compounds are used as electron donor in the preparation of Ziegler-Natta heterogeneous catalysts for the polymerization of olefins.

The alkyl-substituted-1,4-dions derivatives can be suitably obtained via the catalytic hydrogenation, this reaction is well known in the art. A review of this kind of reaction can for example be found in *Comprehensive Organic Transformation: a guide to functional group preparation* by R. C. Larock published by VCH Publishers. Among the various kinds of catalysts which can be used for carrying out this reaction, particularly preferred are the palladium or platinum deposited on carbon, alumina, $BaCO_3$, $CaCO_3$ or $PtO_2$. The content of palladium and platinum for deposited catalyst ranges from 0.5 to 30%, preferably from 1 to 10%. Also usable is the Ni Raney catalyst. The temperature at which this reaction is carried out may range from 0 to 150° C., more typically from 40 to 120° C. The hydrogen pressure is generally higher than the atmospheric pressure and preferably higher than 15 bar. The skilled in the art can easily select, within these ranges, the optimum temperature by taking into account parameters like the boiling temperature of the reaction medium, that of the starting compounds and the like.

Since the 2-alkylidene-1,4 dions derivatives object of the present invention, are intermediates for the preparation of the corresponding alkyl as explained above, even if with the process of the present invention a mixture of isomers of formula (Ia) and (Ib) can be obtained, with the hydrogenation step they become the same compounds and thus the mixture can be used as such without separation of the isomers.

The reaction times for the process of the present invention may be from about 1 min to about 30 hours. More conveniently however, the reaction time is comprised from about 10 min to about 8 hours. In any case, the skilled in the art, can control the state of the reaction by following the techniques known in the art and decide when to stop it.

As explained above this process is very attractive from an industrial standpoint because it allows to obtain the desired product in very good yields and with a minimal work-up. The process of the present invention is also very versatile.

One subclass of compounds obtainable with the process of the invention are diethyl sec-butylidenesuccinate, diethyl cyclopropylidenesuccinate diethyl cyclohexylidenesuccinate, diethyl benzylidenesuccinate, diethyl cyclohexyimethylidenesuccinate, diethyl isobutylidenesuccinate, diethyl isopropylidenesuccinate, diethyl isopentylidenesuccinate and the corresponding products of formula (Ib) and the corresponding compounds esterified with different alkoxy moieties.

When $R^3$ is hydrogen, the 2-alkylidene-1,4-dions derivative obtained with the process of the present invention can be also further substituted on position 3 in a subsequent reaction. The second substitution can be carried out by using the Stobbe reaction, as described for example in EP 01202184.6 with subsequent re-esterification of one acidic group and hydrogenation of the obtained compound.

Thus a further object of the present invention is a process for preparing 2,3-disubstituted-alkylidene-1.4 dions derivatives of formula (IVa), (IVb) or (Ivc) or a mixture thereof:

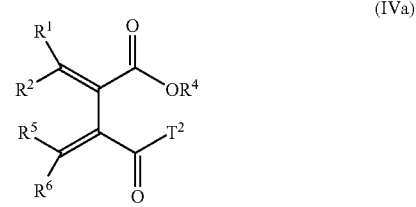

(IVa)

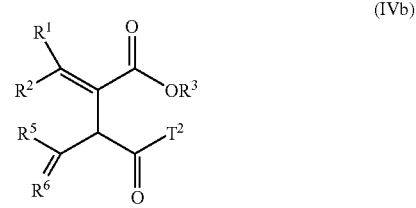

(IVb)

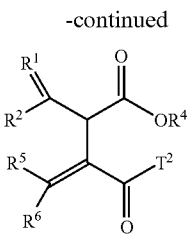

wherein $R^1$, $R^2$ $R^4$ and $T^2$ are described above; preferably $T^2$ is $OR^4$; $R^5$ and $R^6$ equal to or different from each other, are hydrogen atoms or $C_1$-$C_{20}$ hydrocarbon groups; optionally containing heteroatoms belonging to group 13-17 of the periodic table; or $R^5$ and $R^6$ can join together to form a saturated or unsaturated $C_3$-$C_{10}$ ring optionally containing heteroatoms belonging to group 13-17 of the periodic table; with the proviso that $R^5$ and $R^6$ are not hydrogen at the same time;

in the presence of at least one equivalent of a salt of a base or a neutral base at a temperature higher than 70° C.;

comprising the following steps:
a) reacting a compound of formula (II)

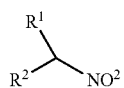

with a compound of formula (Va) or (Vb)

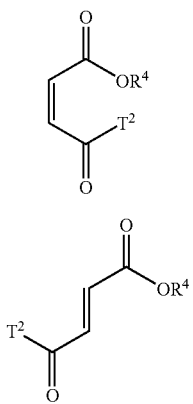

in the presence of at least one equivalent a salts of a base or a neutral base at a temperature higher than 70° C.;
b) treating the compound obtained in step a) with a compound of formula (VI):

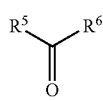

in the presence of a reaction medium and a base; and
c) esterifying the product obtained in step b).

Step a) is substantially equal to the process described above.

Step b) is preferably carried out under conditions such that:
(i) the compound obtained from step a) is used in a molar amount substantially equal to, or lower than, the amount of compound of formula (VI);
(ii) the base used in step b) is in a molar amount substantially equal to the compound obtained in step a) and it is selected from hydrides of formula $MeH_z$, where Me is a metal belonging to group I-II of the periodic table of elements and z is the valence of the metal and alkoxides of formula $R^5OMe$ where $R^5$ is a $C_1$-$C_{15}$ hydrocarbon group and Me has the meaning given above; and
(iii) the reaction medium comprises an aprotic liquid medium or a protic liquid medium having a $K_a$, measured in water, lower than that of iso-propyl alcohol (i-PrOH).

According to the present invention by the term "a molar amount substantially equal" is meant an amount which is no more than 10%, preferably 5%, by mol different from the amount of the compound of reference.

The preferred reaction media for step b) are the aprotic diluents and, among them, toluene, ethylbenzene, xylene, dimethylformammide (DMF), N,N-dimethylacetamide, 1-methyl-2-pyrrolidone, diethylether, tetrahydrofurane are particularly preferred. Toluene and DMF are especially preferred and DMF is the most preferred. Among protic solvents tert-butanol is one of the most preferred. According to the present invention, the reaction medium chosen among aprotic liquid medium or a protic liquid medium having a $K_a$, measured in water, lower than that of i-PrOH, should be the largely prevailing medium but may be not the only one. This means that small amounts (generally not higher than 10% by volume with respect to the total amount of the diluents of liquids not falling within the above classes can in some cases be present for particular purposes. In particular one of these liquids is preferably ethanol.

The base used in step b) is preferably selected among alkoxides of formula $R^7OMe$ where $R^6$ is a $C_1$-$C_{15}$ hydrocarbon group and Me has the meaning given above. Particularly preferred among them are the alkoxides in which $R^6$ is a $C_1$-$C_5$ alkyl group and Me is Na or K. Especially preferred compounds are potassium tert-butoxide, sodium tert-butoxide, potassium ethoxide, sodium ethoxide. As a preferred aspect, such preferred alkoxides are used in combination with the aprotic solvents specified above. In particular the combination of the preferred alkoxides with the aprotic solvents like DMF or toluene is especially preferred.

One class of preferred starting compounds among those of formula (VI) is that in which one of the groups $R^5$ or $R^6$ is hydrogen and the other group is selected from $C_4$-$C_{20}$ hydrocarbon groups, preferably from those not having unsaturation on the carbon atom linked to the carbonyl of formula (VI); particularly preferred are the compounds in which this group is a secondary or tertiary alkyl group. Another class of preferred compounds among those of formula (VI) is that in which both $R^5$ and $R^6$ are $C_1$-$C_{20}$ hydrocarbon groups preferably not having unsaturation on the carbon atom linked to the carbonyl of formula (VI). Among them particularly preferred are the compounds in which $R^5$ and $R^6$ are $C_1$-$C_8$ alkyl groups or $R^5$ and $R^6$ join together to form cyclic ketones. Examples of suitable ketones are methyl ethyl ketone, methyl n-propyl ketone, cyclobutyl methyl ketone, but-3-enyl methyl-ketone, acetylcyclopropane, diethyl ketone, methoxyacetone, isopropyl methyl ketone, 2-hexanone, 4-methyl-2-pentanone, methyl sec-butyl ketone, methyl tert-butyl ketone, ethyl n-propyl ketone, ethyl isopropyl ketone, isopentyl methyl ketone, 4-methylcyclohexanone, 2-methylcyclohexanone, 3-methylcyclohexanone, 2,2-dimethyl-3-pentanone, 2-heptanone, 3-heptanone, di-n-propyl ketone, , dicyclopropyl ketone, di-isopropyl ketone, neo-pentyl methyl ketone, cyclopentyl methyl ketone, 4-methyl-3-hexanone, 1-methyl-butyl methyl ketone, 3-ethyl-2-pentanone, isopropyl n-propyl ketone, 3-methyl-5-hexanone. The compounds in which both $R^5$ and $R^6$ are the same and chosen among methyl, ethyl or propyl are preferred. Also preferred are the compounds in which $R^5$ and $R^6$ are linked together to form cyclic ketones like cyclopentanone, cyclohexanone, or cycloheptanone.

The product of step (b) has a non-esterified carboxylic group formed during this step. In order to transform it into a completely esterified product an esterification step must be carried out which is the step (c) of the process of the invention. The esterification step can be carried out according to any of the many methods known in the art. One of the known methods for obtaining esters includes for example the esterification of a carboxylic acid through the reaction with an alcohol catalyzed by an acid or a base. A comprehensive review of many methods for preparing the esters can be found in *Organic Functional Group Preparation, II Edition, Academic Press* 1983. The preferred method for carrying out the esterification according to the present invention is the reaction of the product of step (b) with a compound of formula $R^8X$ where X is halogen and $R^8$ is $C_1$-$C_{20}$ hydrocarbon group. Preferably, X is selected from Br, Cl and I and $R^7$ is a primary $C_1$-$C_8$ alkyl group. Particularly preferred $R^8$ groups are methyl, ethyl, n-propyl, n-butyl and isobutyl. The use of ethyl bromide is especially preferred. This method has the advantage that the alkylidene substituted product of step (b) can directly be reacted with the compound of formula $R^8X$ without being first subjected to a preliminary work-up thereby saving time and increasing the yields. The temperature for carrying out step (c) is not critical. It generally ranges from about –30 to 150° C., more typically from –10 to 110° C. The skilled in the art can easily select, within these ranges, the optimum temperature by taking into account parameters like the boiling temperature of the reaction medium, that of the starting compounds and the like.

Preferably in the above described process all steps a), b) and c) are carried out "one pot" i.e. without isolating the intermediate products.

The product of formula (IVa) or (IVb) or (IVc) is subsequently subjected to a hydrogenation step as described above. Thus, since these products are intermediates for the preparation of 2,3-dialkyl-substituted derivatives of succinic and 4-oxo-butanoic acids, even if with the process of the present invention a mixture of isomers of formula (IVa), (IVb) and (IVc) can be obtained, with the hydrogenation step they become the same compounds and thus the mixture can be used as such without separation of the isomers.

The saturated derivatives of succinic and 4-oxo-butanoic acids, object of the present invention, find various applications in the art including the use in the pharmaceutical industry and, as mentioned above, as modifying compounds of Ziegler-Natta polymerization catalysts.

The following examples are given in order to illustrate and not limit the invention.

EXAMPLES

Analytical gas chromatography was performed on Hewlett Packard 6890 GC (Hewlett Packard HP-5, 30 m×0.53 mm×0.88 μm with Packed Inlet and/or Restek Rtx-200, 30 m×0.53 mm×0.50 μm with Cool On-Column Inlet) using flame ionization detector. Final products have been characterized by $^1$H NMR (Varian Unity 300 Spectrometer, 300 MHz) and GC/MS (Hewlett Packard 6890 GC with Hewlett Packard 5973 Mass Selective Detector).

Examples 1-3

Synthesis of a Mixture of 2-Isopropylidene-Succinic Acid Diethyl Ester (1) and 2-Isopropenyl-Succinic Acid Diethyl Ester (2) from Maleic Acid Diethyl Ester (3) in Different Solvents

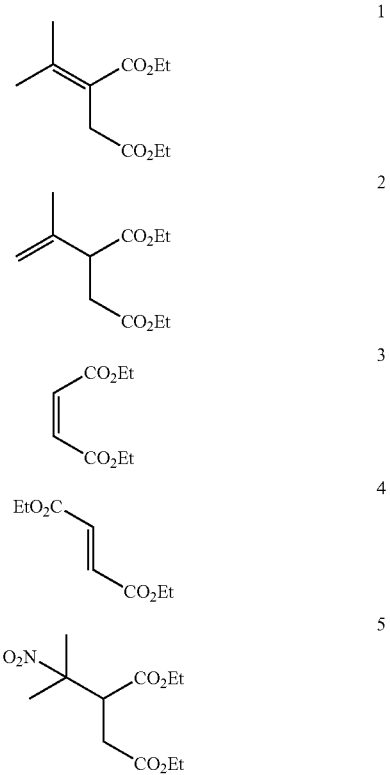

A mixture of potassium carbonate (Aldrich, powder, –325 mesh, not anhydrous, 98+%; 49.5 mmol), an organic sovent (15.0 ml), maleic acid diethyl ester (45.0 mmol), and 2-nitropropane (47.3 mmol) was heated up fast, in 7 min., to a reflux temperature and stirred under reflux until the completion of the reaction according to GC-analysis. All the reactions gave a mixture of two isomeric products 1 and 2 in very high yields without impurities due to maleic acid diethyl ester (3), fumaric acid diethyl ester (4) (product of isomerization of the starting maleic acid diethyl ester which is formed in the course of the reaction), or 2-(1-methyl-1-nitro-ethyl)-succinic acid diethyl ester (5) (intermediate product formed during the reaction). Solvents used, boiling points of the solvents, reaction times, relative amounts of the products 1 and 2, and the combined yields of these products are reported in table 1 below (relative amounts of the products and yields were established by GC; for determination of the yields an internal standard technique was used).

TABLE 1

| Ex. | Solvent | B.P. of Solvent, °C. | Reaction Time, h | Ratio 1/2 | Combined Yield (1 + 2), % |
|---|---|---|---|---|---|
| 1 | N,N-Dimethylformamide | 153 | 1 | 92/8 | 98 |
| 2 | Diglyme | 162 | 3 | 89/11 | 94 |
| 3 | o-Xylene | 143-145 | 20 | 88/12 | 96 |

Example 4

Synthesis of a Mixture of 2-Isopropylidene-Succinic Acid Diethyl Ester (1) and 2-Isopropenyl-Succinic Acid Diethyl Ester (2) from Fumaric Acid Diethyl Ester (4)

A mixture of potassium carbonate (Aldrich, powder, −325 mesh, not anhydrous, 98+%; 49.5 mmol), N,N-dimethylformamid (15.0 ml), fumaric acid diethyl ester (45.0 mmol), and 2-nitropropane (47.3 mmol) was heated up fast to a reflux temperature and stirred under reflux for 0.5 h to give a 89/11-mixture of two isomeric products 1 and 2 with a combined yield of 92% without impurities due to maleic acid diethyl ester (3), fumaric acid diethyl ester (4), or 2-(1-methyl-1-nitro-ethyl)-succinic acid diethyl ester (5) (relative amounts of the products and yields were established by GC; for determination of the yields an internal standard technique was used).

Example 5

Synthesis of 2.3-Diisopropylidene-Succinic Acid Diethyl Ester (6) from Maleic Acid Diethyl Ester (3) by One-Pot Approach

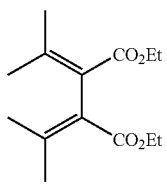

6

Potassium carbonate (Aldrich, powder, −325 mesh, not anhydrous, 98+%; 240 mmol), N,N-dimethylformamid (133 ml), maleic acid diethyl ester (400 mmol) and 2-nitropropane (408 mmol) were placed at room temperature in a 1L round bottom 4-neck flask fitted with a mechanical stirrer, a reflux condenser, and a thermocouple. The reaction mixture was brought fast, in 10 min., to a reflux and stirred at reflux for 50 min. After cooling to 75° C. from 150° C., the temperature reached by the mixture in the end of 50 min. of reflux, the reaction mixture was treated with toluene (130 ml) during 8 min. A toluene-water mixture (125 ml) was slowly distilled off during 60 min. while gradually increasing the temperature of the reaction mixture from 75° C. back to 150° C. After cooling to 30° C., the mixture was treated with acetone (432 mmol) added fast in one portion and then with potassium ethoxide (460 mmol) added during 15 min. using a powder addition funnel. The funnel was rinsed with N,N-dimethylformamid (5×10 ml) to transfer all the potassium ethoxide into the reaction flask. After that the reaction mixture was heated to 60° C. and stirred for 30 min. The mixture was then treated with bromoethane (460 mmol) added fast in one portion, warmed up to 80° C., and stirred at 80° C. for 60 min. Following cooling to 60° C., the reaction mixture was treated subsequently with acetone (32.0 mmol) and potassium ethoxide (100 mmol) both added in one portion, stirred for 30 min., then heated up to 80° C., treated at this temperature with bromoethane (216 mmol) added fast in one portion, and stirred at the same temperature for additional 60 min. Upon completion of the reaction, the mixture was cooled to 10° C., quenched with water (333 ml), and then diluted with ether (133 ml). The organic phase was separated and the water phase was extracted with ether (5×100 ml). The combined organic phases were washed three times with water (1×157 ml, 1×100 ml, 1×77 ml), concentrated on a rotary evaporator, and distilled in vacuum (flash distillation) to give 94.4 g of the product (93% yield).

Example 6

Synthesis of 2,3-Diisopropylidene-Succinic Acid Diethyl (6) from Maleic Acid Diethyl Ester (3) by One-Pot Approach Potassium carbonate (Aldrich, powder, −325 mesh, not anhydrous, 98+%; 240 mmol), N,N-dimethylformamid (133 ml), maleic acid diethyl ester (400 mmol) and 2-nitropropane (408 mmol) were placed at room temperature in a 1L round bottom 4-neck flask fitted with a mechanical stirrer, a reflux condenser, and a thermocouple. The reaction mixture was brought fast, in 8 min., to a reflux and stirred at reflux for 52 min. After cooling to 110° C. from 150° C., the temperature reached by the mixture in the end of 52 min. of reflux, the reaction mixture was treated with toluene (50 ml) added fast in one portion. The reaction flask was then fitted with a 20 ml Dean-Stark receiver, the mixture was heated up to a reflux temperature (~140° C.) and the water formed during the first stage of the reaction was removed by azeotropic drying total 51 ml of a toluene-water mixture were collected during the azeotropic drying and the subsequent distillation. After cooling to 60° C., the reaction mixture was treated with acetone (432 mmol) added fast in one portion, then with a solution of potassium ethoxide (460 mmol) in a mixture of N,N-dimethylformamide (153 ml) and ethanol (26.7 ml) added dropwise during 10 min., and following the completion of the addition stirred at 60° C. for 30 min. The mixture was then treated with bromoethane (460 mmol) added fast in one portion, heated up from 60° C. to 80° C., and stirred at this temperature for 60 min. After that the reaction mixture was treated with potassium ethoxide (100 mmol) added fast in one portion, stirred for 30 min., then treated with bromoethane (216 mmol) added fast in one portion, and stirred at the same temperature of 80° C. for additional 60 min. Upon completion of the reaction, the mixture was cooled to 10° C., quenched with water (333 ml), and then diluted with ether (133 ml). The organic phase was separated and the water phase was extracted with ether (4×100 ml). The combined organic phases were washed three times with water (1×157 ml, 1×100 ml, 1×77 ml), concentrated on a rotary evaporator, and distilled in vacuum (flash distillation) to give 92.4 g of the product (91% yield).

Comparative Example 1

Synthesis of a Mixture of 2-Isopropylidene-Succinic Acid Diethyl Ester (1) and 2-Isopropenyl-Succinic Acid Diethyl Ester (2) from Maleic Acid Diethyl Ester (3)

A solution of 2-nitropropane (3.90 mmol) and maleic acid diethyl ester (3.00 mmol) in acetonitrile (6.0 ml) was treated with DBU (3.30 mmol) added fast in one portion at room temperature. After stirring for 0.5 h at this temperature, the reaction mixture was evaporated, and then analysed. A 92/8-mixture of two isomeric products 1 and 2 with a combined yield of 81% was obtained accompanied by impurities due to maleic acid diethyl ester (3), fumaric acid diethyl ester (4), and 2-(1-methyl-1-nitro-ethyl)-succinic acid diethyl ester (5); the ratio of the products 1/2/3/4/5 was 89.1/7.6/2.5/0/0.8 (relative amounts of the products and yields were established by GC; for determination of the yields an internal standard technique was used).

Comparative Example 2

Synthesis of a Mixture of 2-Isopropylidene-Succinic Acid Diethyl Ester (1) and 2-Isopropenyl-Succinic Acid Diethyl Ester (2) from Maleic Acid Diethyl Ester (3)

A solution of 2-nitropropane (5.00 mmol) and maleic acid diethyl ester (5.00 mmol) in acetonitrile (20 ml) was treated with DBU (5.00 mmol) added fast in one portion at room temperature. After stirring for 4.5 h, the reaction mixture was treated with additional 2-nitropropane (0.502 mmol) and DBU (0.502 mmol), stirred at room temperature overnight, and then analysed. Reaction times and relative amounts of the products 1, 2, 3, 4, and 5 are reported in the table 2 below. In the end of the reaction a 95/5-mixture of two isomeric products 1 and 2 with a combined yield of 85% was obtained accompanied by impurities due to maleic acid diethyl ester (3), fumaric acid diethyl ester (4), and 2-(1-methyl-1-nitro-ethyl)-succinic acid diethyl ester (5) (relative amounts of the products and yields were established by GC; for determination of the yields an internal standard technique was used).

TABLE 2

| Reaction Time, h | Ratio 1/2/3/4/5 | Yield of 1, % | Yield of 2, % |
|---|---|---|---|
| 10 min | 5.8/0.2/41.5/0.2/52.3 | — | — |
| 3 | 65.1/1.4/9.4/0.8/23.3 | 41 | 1 |
| 6 | 78.3/2.4/5.8/0.6/12.9 | 59 | 2 |
| overnight | 91.4/4.8/1.2/0.2/2.4 | 81 | 4 |

The invention claimed is:

1. A process for the preparation of 2-alkylidene-1,4-dions derivatives of formula (Ia) or (Ib) or a mixture of (Ia) and (Ib):

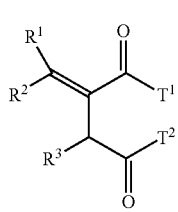

(Ia)

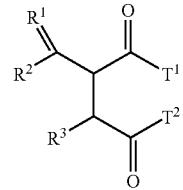

(Ib)

wherein $R^1$, $R^2$ and $R^3$, equal to or different from each other, are hydrogen atoms or $C_1$-$C_{20}$ hydrocarbon groups, optionally containing heteroatoms belonging to group 13-17 of the periodic table, or $R^1$ and $R^2$ can join together to form a saturated or unsaturated $C_3$-$C_{10}$ ring, optionally containing heteroatoms belonging to group 13-17 of the periodic table, with the proviso that when $R^1$ and $R^2$ are both hydrogen atoms, only compounds of formula (Ia) are obtained;

$T^1$ and $T^2$, equal to or different from each other, are H, $OR^4$, $R^4$, $NR^4{}_2$, $SR^4$ or $PR^4{}_2$, or $T^1$ and $T^2$ can be fused in an oxygen atom or a $NR^4$ group;

$R^4$, equal to or different from each other, are a $C_1$-$C_{20}$ hydrocarbon group, optionally containing one or more heteroatoms belonging to group 13-17 of the periodic table;

said process comprising the step of reacting a compound of formula (II):

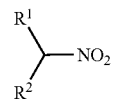

(II)

with a compound of formula (IIIa) or (IIIb):

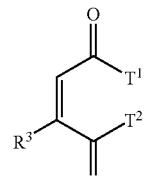

(IIIa)

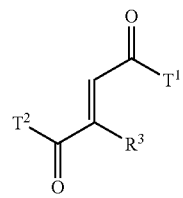

(IIIb)

in the presence of at least one equivalent with respect to the compound of formula (IIIa) or (IIIb) of a salt of a base or a neutral base at a temperature higher than 70° C.

2. The process according to claim 1 wherein the salt of a base or a neutral base is:

(i) oxides of metals belonging to groups 1-13 of the periodic table;

(ii) compounds of formula $NR^9_3$ wherein $R^9$, equal to or different from each other, are hydrogen atoms, or a linear or branched, saturated or unsaturated, $C_1$-$C_{10}$ alkyl, $C_6$-$C_{20}$aryl, $C_7$-$C_{20}$ arylalkyl or $C_7$-$C_{20}$ alkylaryl groups, optionally containing O, S, N, P, Si or halogen atoms, or two or more $R^9$ form one or more saturated or unsaturated 4 to 7 membered rings, optionally containing O, S, N, P or Si atoms, that can bear substituents, and when this ring is aromatic, one $R^9$ can also be a bond part of a double bond;

(iii) compounds of formula $MT_j$, wherein M is a metal of groups 1-12 of the periodic table, or a group $(NR^9_4)^+$; T is H, $F^-$, $OH^-$, $HCO3^-$, $RO^-$ or $RC(O)O^-$ wherein R is a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radical, optionally containing one or more halogen atoms; j is equal to the valence of the metal M or 1 in the case M is $(NR^9_4)^+$; or (iv) carbonates of metal M.

3. The process according to claim 1 wherein $R^3$ is a hydrogen atom, a linear or secondary $C_1$-$C_8$ alkyl or a $C_5$-$C_7$ cycloalkyl group.

4. The process according to claim 3 wherein $R^3$ is a hydrogen atom.

5. The process according to claim 1 wherein $R^4$ is a linear or branched $C_1$-$C_{20}$ alkyl, $C_3$-$C_{10}$ cycloalkyl, $C_6$-$C_{10}$ aryl or a $C_7$-$C_{12}$ alkylaryl group, and $T^1$ and $T^2$ are an $OR^4$ group.

6. The process according to claim 2 wherein M is a metal of groups 1, 2 of the periodic table.

7. The process according to claim 1 wherein the salt is a carbonate of metal M, wherein M is a metal of groups 1-12 of the periodic table.

8. The process according to claim 1 wherein said process is carried out at a temperature from 80 to 220° C.

9. The process according to claim 8 wherein the temperature ranges from 150 to 200° C.

10. The process according to claim 1 wherein in the compounds of formula (Ia) or (Ib), $R^2$ is hydrogen and $R^1$ is selected from $C_4$-$C_{20}$ hydrocarbon groups.

11. The process according to claim 1 wherein in the compounds of formula (Ia) or (Ib), $R^1$ and $R^2$ are $C_1$-$C_{20}$ hydrocarbon groups.

12. The process according to claim 11 wherein in the compounds of formula (Ia) or (Ib), $R^1$ and $R^2$ are $C_1$-$C_8$ alkyl.

13. A process for preparing 2,3-disubstituted-alkylidene-1,4 dions derivatives of formula (IVa), (IVb) or (IVc) or a mixture thereof:

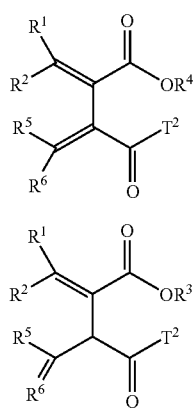

(IVa)

(IVb)

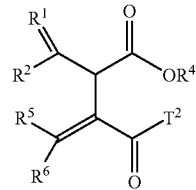

(IVc)

wherein $R^1$ and $R^2$, equal to or different from each other, are hydrogen atoms or $C_1$-$C_{20}$ hydrocarbon groups, optionally containing heteroatoms belonging to group 13-17 of the periodic table, or $R^1$ and $R^2$ can join together to form a saturated or unsaturated $C_3$-$C_{10}$ ring, optionally containing heteroatoms belonging to group 13-17 of the periodic table, with the proviso that when $R^1$ and $R^2$ are both hydrogen atoms, only compounds of formula (IVa) or (IVb) are obtained;

$T^2$ is H, $OR^4$, $R^4$, $NR^4_2$, $SR^4$ or $PR^4_2$;

$R^4$, equal to or different from each other, are a $C_1$-$C_{20}$ hydrocarbon group, optionally containing one or more heteroatoms belonging to group 13-17 of the periodic table;

$R^5$ and $R^6$, equal to or different from each other, are hydrogen atoms or $C_1$-$C_{20}$ hydrocarbon groups, optionally containing heteroatoms belonging to group 13-17 of the periodic table, or $R^5$ and $R^6$ can join together to form a saturated or unsaturated $C_3$-$C_{10}$ ring, optionally containing heteroatoms belonging to group 13-17 of the periodic table; with the proviso that $R^5$ and $R^6$ are not hydrogen at the same time;

said process comprising the following steps:

a) reacting a compound of formula (II)

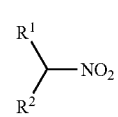

(II)

with a compound of formula (Va) or (Vb)

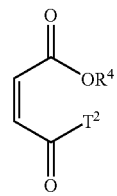

(Va)

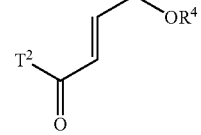

(Vb)

in the presence of at least one equivalent with respect to the compound of formula (Va) or (Vb) of a salt of a base or a neutral base at a temperature higher than 70° C.;

b) treating the compound obtained in step a) with a compound of formula (VI):

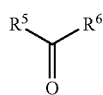

in the presence of a reaction medium and a base; and c) esterifying the product obtained in step b).

14. The process according to claim 13 wherein the salt of a base or a neutral base used in step a) is:
   (i) oxides of metals belonging to groups 1-13 of the periodic table;
   (ii) compounds of formula $MT_j$ wherein M is a metal of groups 1-12 of the periodic table; T is H, $OH^-$, $HCO3^-$, $RO^-$ or $RC(O)O^-$ wherein R is a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radical, optionally containing one or more halogen atoms; and j is equal to the valence of the metal M;
   (iii) compounds of formula $NR^9_3$ wherein $R^9$, equal to or different from each other, are hydrogen atom, or a linear or branched, saturated or unsaturated, $C_1$-$C_{10}$ alkyl, $C_6$-$C_{20}$ aryl, $C_7$-$C_{20}$ arylalkyl or $C_7$-$C_{20}$ alkylaryl groups, optionally containing O, S, N, P, Si or halogen atoms, or two or more $R^9$ form one or more $C_4$-$C_7$ rings; or
   (iv) carbonates of metal M.

15. The process according to claim 13 wherein
   (i) the compound obtained from step a) is used in a molar amount at most 10% higher than the amount of compound of formula (VI);
   (ii) the base used in step b) is in a molar amount from 10% higher than to 10% lower than the amount of the compound obtained in step a) and it is selected from hydrides of formula $MeH_z$ wherein Me is a metal belonging to groups 1 and 2 of the periodic table of elements and z is the valence of the metal and alkoxides of formula $R^7OMe$ wherein $R^7$ is a $C_1$-$C_{15}$ hydrocarbon group; and
   (iii) the reaction medium comprises an aprotic liquid medium or a protic liquid medium having a $K_a$, measured in water, lower than that of iso-propyl alcohol (I-PrOH).

16. The process according to claim 13 wherein in step c) the product of step (b) is reacted with a compound of formula $R^8X$ wherein X is halogen and $R^8$ is $C_1$-$C_{20}$ hydrocarbon group.

17. The process according to claim 13 wherein step a) is carried out at a temperature from 80 to 220° C.

18. The process according to claim 17 wherein step a) is carried out at a temperature range from 150 to 200° C.

19. The process according to claim 13 wherein all steps a), b) and c) are carried out without isolating the intermediate products.

20. The process according to claim 13 wherein one of the groups $R^5$ or $R^6$ is hydrogen and the other group is selected from $C_4$-$C_{20}$ hydrocarbon groups.

21. The process according to claim 13 wherein both $R^5$ and $R^6$ are $C_1$-$C_{20}$ hydrocarbon groups.

22. The process according to claim 3 wherein $R^3$ is methyl, ethyl, isobutyl or cyclohexyl.

* * * * *